(12) United States Patent
Spahn et al.

(10) Patent No.: US 9,357,963 B1
(45) Date of Patent: Jun. 7, 2016

(54) GRAYSCALE THERMOGRAPHIC IMAGING

(76) Inventors: James G. Spahn, Carmel, IN (US);
Kadambari Nuguru, Indianapolis, IN (US)

( * ) Notice: Subject to any disclaimer, the term of this patent is extended or adjusted under 35 U.S.C. 154(b) by 740 days.

(21) Appl. No.: 13/439,177

(22) Filed: Apr. 4, 2012

Related U.S. Application Data

(60) Provisional application No. 61/516,459, filed on Apr. 4, 2011.

(51) Int. Cl.
*A61B 6/00* (2006.01)
*A61B 5/00* (2006.01)
(52) U.S. Cl.
CPC ..................................... *A61B 5/445* (2013.01)

(58) Field of Classification Search
CPC .... A61B 5/445; A61B 5/0075; A61B 5/0261;
A61B 5/0059; A61B 5/0077; A61B 5/0062;
A61B 5/015; A61B 5/01; A61B 18/20;
G01N 21/3581; G01N 21/359; G01N 21/71;
G06T 7/0012; G06T 2207/10036; H04N 5/332
See application file for complete search history.

(56) References Cited

U.S. PATENT DOCUMENTS

2005/0033145 A1* 2/2005 Graham et al. ............... 600/407

* cited by examiner

*Primary Examiner* — Elmer Chao
(74) *Attorney, Agent, or Firm* — Jacque R. Wilson; Carson Boxberger LLP

(57) ABSTRACT

Through the measurement and interpretation of the pixels of grayscale digital thermographic images of abnormalities of the skin and its subcutaneous tissue, early intervention and treatment of abnormalities of the skin and its subcutaneous tissue are possible, thereby assisting clinicians in making significant impacts on prevention and treatment.

12 Claims, 21 Drawing Sheets

| | LIR | Digital Visual |
|---|---|---|
| Monitors | LIR thermal intensity gradiency | Visible light |
| Measures | Physiologic status view | Anatomical view |
| Benefits | Recognition of skin and soft tissue abnormalities prior to clinical recognition | Image that represents the visual status of skin and/or subcutaneous tissue |
| | Creates awareness of site with abnormality to allow sequential evaluation of a condition | Identifies visually the site where the IR image is either normal or abnormal |
| | Documentation of LIR thermal presenting the findings in a trending fashion | Documentation of visual presentation of the findings in a trending fashion |

FIG. 1

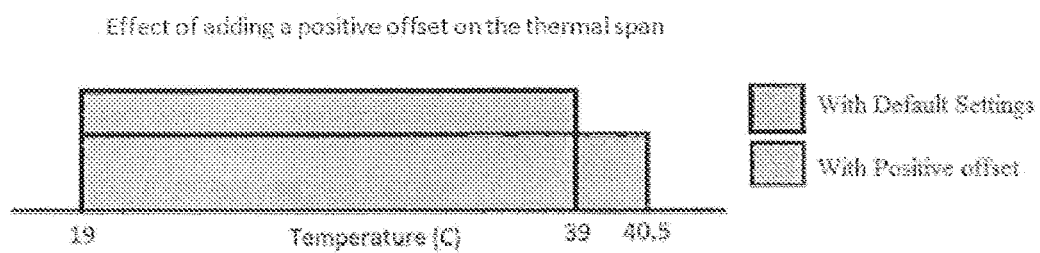
FIG. 2.1

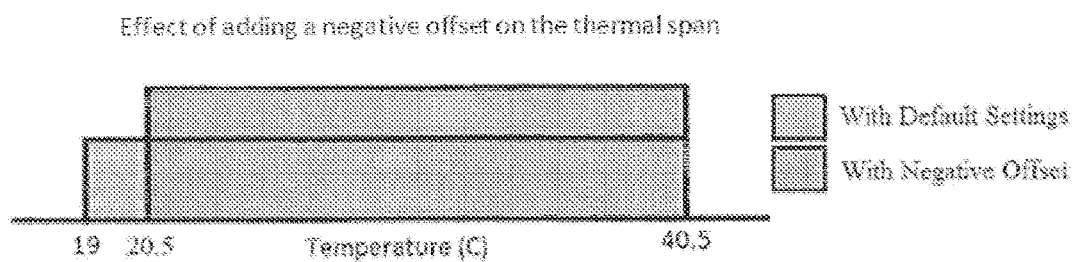
FIG. 2.2

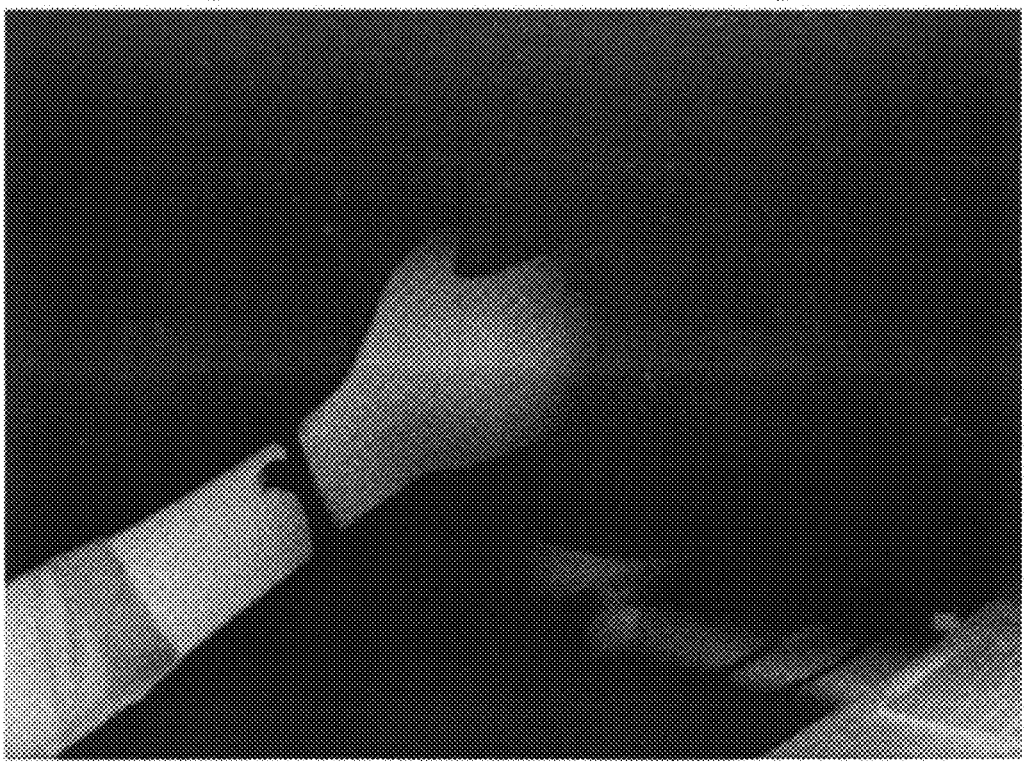
FIG. 2.3

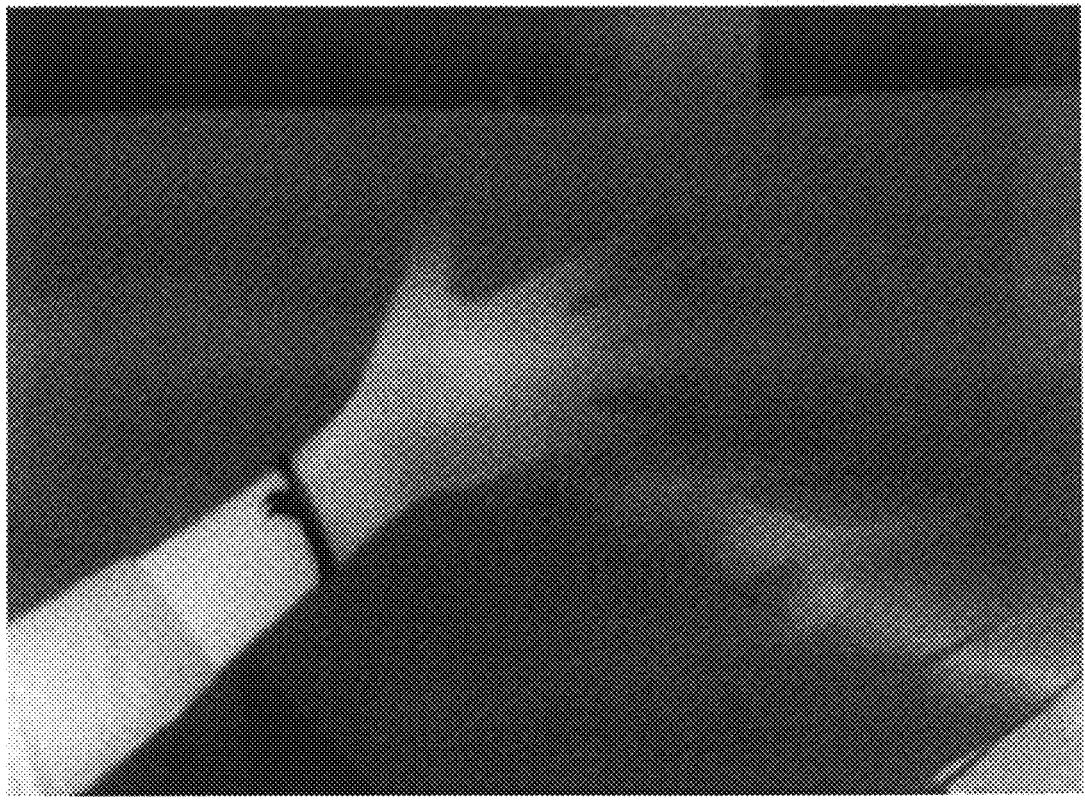
Fig. 2.4

Original Image　　　　　Zoomed Image

\* symbol represents the wound base point selection made for a thermal image

| Wound base Selection | Gray Scale Value |
|---|---|
| 1 | 62 |
| 2 | 48 |
| 3 | 41 |
| 4 | 26 |

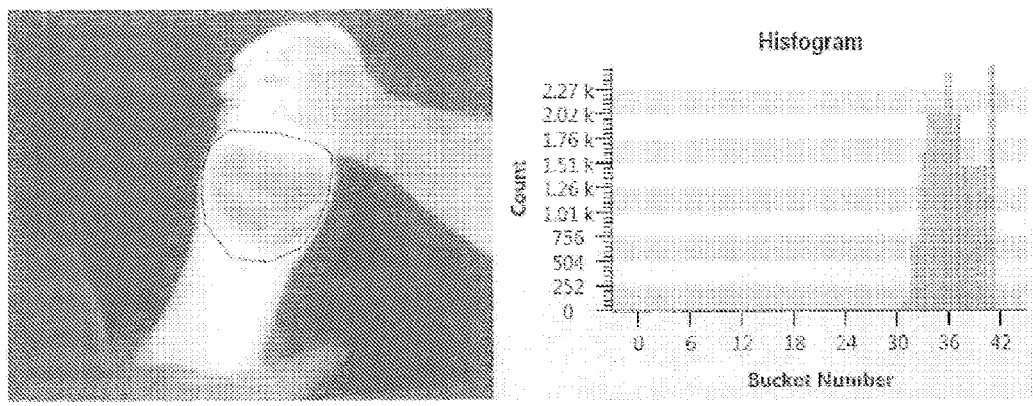
FIG. 13.1
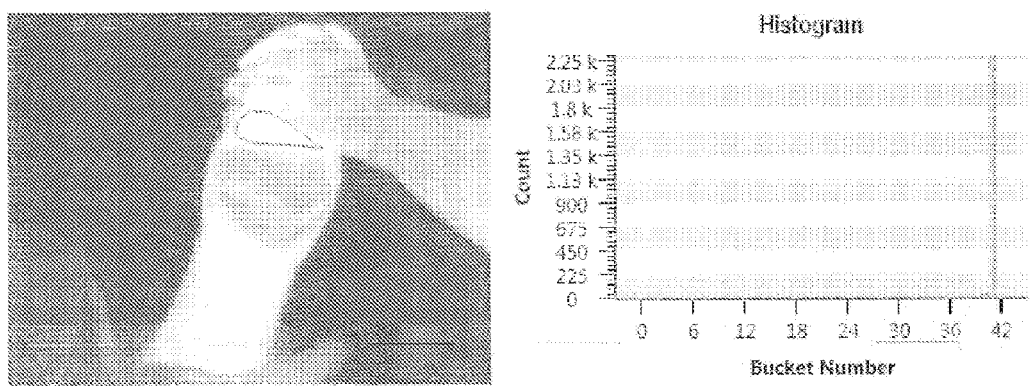
FIG. 13.2

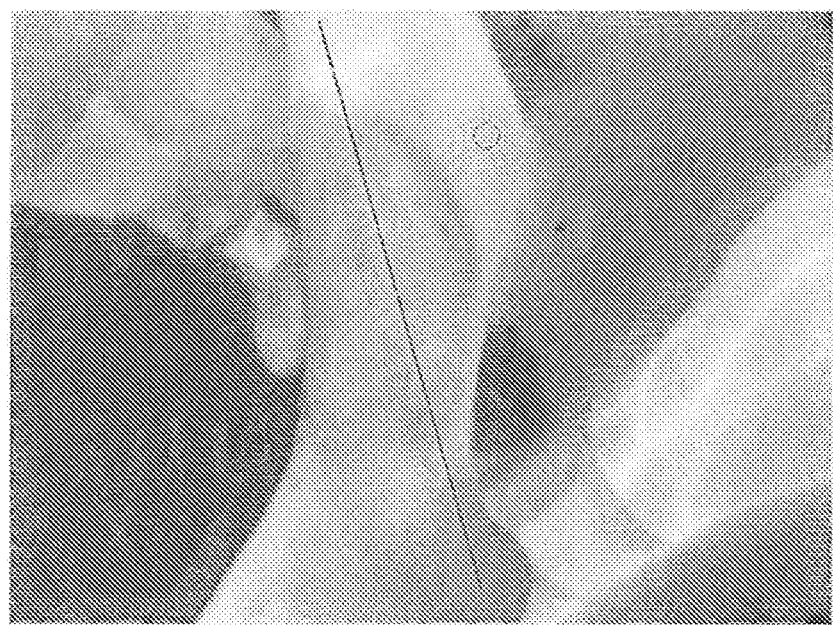
FIG. 15.1

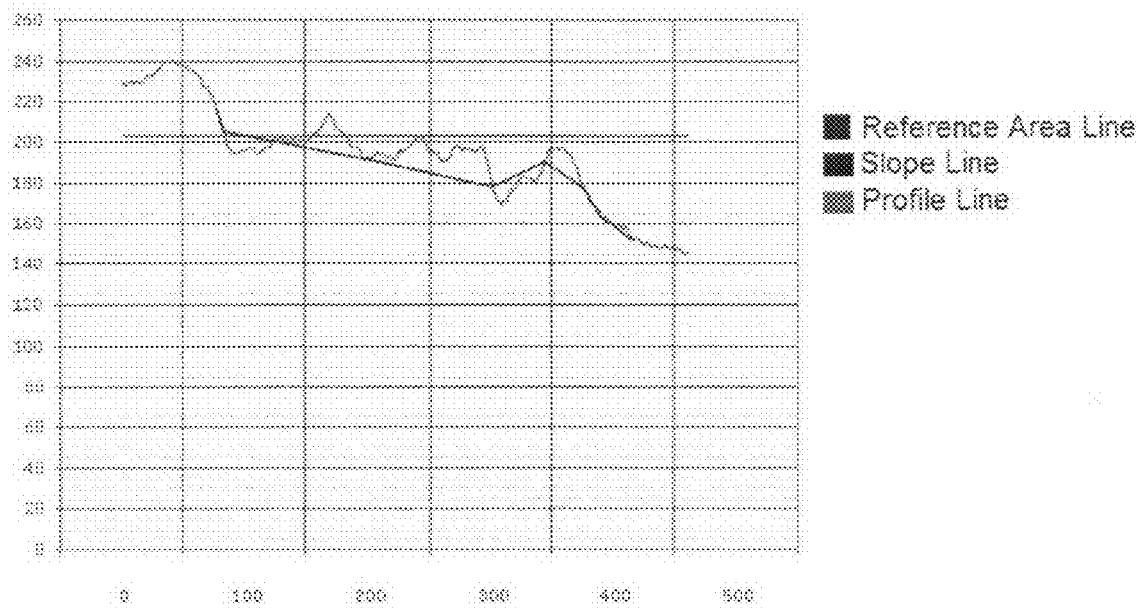
FIG. 15.2

GRAYSCALE THERMOGRAPHIC IMAGING

CROSS-REFERENCE TO RELATED APPLICATIONS

The present application claims priority to U.S. Provisional Patent Application 61/516,459, filed Apr. 4, 2011.

BACKGROUND OF THE INVENTION

Over the last century, clinicians, which term includes herein certified and licensed medical doctors of all specialties, osteopathic doctors of all specialties, podiatrists, dental doctors of all specialties, chiropractors, veterinarians of all specialties, nurses, and medical imaging technicians, have become dependent on the use of medical devices that assist them in their delivery of patient-centered care. The common function of these devices is to assist and not replace the clinical judgment of the clinician. This fulfills the dictum that best practice is clinical judgment assisted by scientific data and information.

Entering into the era of computer science and sophisticated electronics, clinicians have the opportunity to be supported by data and information in a statistically significant and timely fashion. These advancements have allowed more extensive and useful collection of meaningful data that can be acquired, analyzed, and applied in conjunction with the knowledge and expertise of the clinician.

Medical long-wave infrared (LIR) thermography has been known to be beneficial in the evaluation of thermal heat intensity and gradiency relating to abnormalities of the skin and subcutaneous tissue (SST). Although this technology has expanded to other areas of medical evaluation, the scope of this patent application is limited to the SST abnormalities. These abnormalities include the formation of deep tissue injury (DTI) and subsequent necrosis caused by mechanical stress, infection, auto-immune condition, and vascular flow problems. DTI caused by mechanical stress (pressure, shear and frictional forces) can be separated into three categories. The first category is a high magnitude/short duration mechanical stress represented by traumatic and surgical wounds. The second category is low magnitude/long duration mechanical stress represented by pressure ulcer development, which is also a factor in the development of ischemic and neuropathic wounds. The third category is a combination of categories one and two represented by pressure ulcer formation in the bariatric patient.

The pathophysiologic conditions that occur with DTI and subsequent necrosis of the affected tissue are ischemia, cell distortion, impaired lymphatic drainage, impaired interstitial fluid flow, and reperfusion injury. Category one is dominated by cell distortion and even destruction. Category two is dominated by ischemia. Category three is a combination of cell distortion and ischemia.

Hypoxia causes aerobic metabolism to convert to anaerobic metabolism. This occurrence causes lactic acidosis followed by cell destruction, release of enzymes and lytic reactions. The release of these substances causes additional cell injury and destruction, and initiation of the inflammatory response.

It is very important to recognize that ischemic-reperfusion injury is associated with all of the above mechanical stress induced SST injuries. This condition is caused by a hypoxia induced enzymatic change and the respiratory burst associated with phagocytosis when oxygen returns after an ischemic event. The result of ischemic-reperfusion injury is the formation of oxygen free radicals (hydroxyl, superoxide, and hydrogen peroxide) that cause damage to healthy and already injured cells leading to extension of the original injury SST injury and subsequent necrosis can also be caused by vascular disorders. Hypoxia can be caused by an arterial occlusion or by venous hypertension. Lymphatic flow or node obstruction can also create vascular induced injury by creating fibrous restriction to venous drainage and subsequent cellular stasis in the capillary system. These disorders are also accentuated by reperfusion injury and oxygen free radical formation.

Infection of the skin (impetigo), subcutaneous tissue (cellulitis), deep tissue (fasciitis), bone (osteomyelitis) and cartilage (chondritis) causes injury and necrosis of the affected tissue. Cells can be injured or destroyed by the microorganism directly, by toxins released by the microorganism and/or the subsequent immune and inflammatory response. These disorders are also accentuated by reperfusion injury and oxygen free radical formation.

Auto-immune morbidities of the skeletal joints (rheumatoid arthritis), subcutaneous tissue (tendonitis, myelitis, dermatitis) and blood vessels (vasculitis) cause similar dysfunction and necrosis of the tissue being affected by the hypersensitivity reactions on the targeted cells and the subsequent inflammatory response. Again, these conditions are accentuated by reperfusion and oxygen free radical formation.

The common event that addresses all of the above SST injuries is the inflammatory response. This response has two stages. The first stage is vascular and the second is cellular. The initial vascular response is vasoconstriction that will last a short time. The constriction causes decrease blood flow to the area of injury. The decrease in blood flow causes vascular "pooling" of blood (passive congestion) in the proximal arterial vasculature in the region of injury and intravascular cellular stasis occurs along with coagulation.

The second vascular response is extensive vasodilation of the blood vessels in the area of necrosis. This dilation along with the "pooled" proximal blood causes increased blood flow with high perfusion pressure into the area of injury. This high pressure flow can cause damage to endothelial cells. Leakage of plasma, protein, and intravascular cells causes more cellular stasis in the capillaries (micro-thrombotic event) and hemorrhage into the area of injury. When the perivascular collagen is injured, intravascular and extravascular coagulation occurs. The rupture of the mast cells causes release of histamine that increases the vascular dilation and the size of the junctions between the endothelial cells. This is the beginning of the cellular phase. More serum and cells (mainly neutrophils) enter into the area of the mixture of injured and destroyed cells by the mechanism of marginalization, emigration (diapedesis) and the chemotaxic recruitment (chemotaxic gradiency). Stalling of the inflammatory stage can cause the area of necrosis (ring of ischemia) to remain in the inflammatory stage long past the anticipated time of 2-4 days. This continuation of the inflammatory stage leads to delayed resolution of the ischemic necrotic event.

The proliferation stage starts before the inflammatory stage recedes. In this stage angiogenesis occurs along with formation of granulation and collagen deposition. Contraction occurs, and peaks, at 5-15 days post injury.

Re-epithelialization occurs by various processes depending on the depth of injury. Partial thickness wounds can resurface within a few days. Full thickness wounds need granulation tissue to form the base for re-epithelialization to occur. The full thickness wound does not heal by regeneration due to the need for scar tissue to repair the wound. The repaired scarred wound has less vascularity and tensile strength of normal regional uninjured SST. The final stage is remodeling. In this stage the collagen changes from type III to a stronger type I and is rearranged into an organized tissue.

All stages of wound healing require adequate vascularization to prevent ischemia, deliver nutrients, and remove metabolic waste. Following the vascular flow and metabolic activity of a necrotic area is currently monitored by patient assessment and clinical findings of swelling, pain, redness, increased temperature, and loss of function.

SUMMARY OF THE INVENTION

Medical devices are now available to assist the clinician in defining the presence, type, and status of the SST injury. The LIR thermal and digital imaging device is a non-contact and non-radiating device that can be utilized bedside. The combination of imagers allows both visible and invisible radiation from the body to be evaluated. (See FIG. 1) This allows both the anatomical and physiologic status of the SST to be evaluated for injuries or disorders that are not yet clinically recognizable. By visualizing the IR thermal intensity, the clinician can evaluate the gradiency of the long-wave radiation emitted from the body region being imaged. The ability to visualize the thermal gradiency allows the clinician to evaluate the metabolic activity and blood flow of the region being imaged. The normal SST can be used as a control for that specific imaging procedure.

Having a real time control allows an area of interest (AOI) to be recognized. The AOI can be of greater intensity (hotter) or less intensity (cooler) than the normal SST of that region of the body. The AOI can then be evaluated by the clinician for the degree of metabolism, blood flow, necrosis, inflammation and the presence of infection by comparing the warmer or cooler thermal intensity of the AOI or wound base and peri-AOI or wound area to the normal SST of the location being imaged. Serial imaging also can assist the clinician in the ability to recognize improvement or regression of the AOI or wound over time.

The use of an LIR thermal and digital visual imager can be a useful adjunct tool for clinicians with appropriate training to be able to recognize physiologic and anatomical changes in an AOI before it presents clinically and also the status of the AOI/wound in a trending format. By combining the knowledge obtained from the images with a comprehensive assessment, skin and subcutaneous tissue evaluation, and an AOI or wound evaluation will assist the clinician in analyzing the etiology, improvement or deterioration, and the presence of infection affecting the AOI or wound.

The foundational scientific principles behind LIR thermography technology are energy, heat, temperature, and metabolism.

Energy is not a stand-alone concept. Energy can be passed from one system to another, and can change from one form to another, but can never be lost. This is the First Law of Thermodynamics. Energy is an attribute of matter and electromagnetic radiation. It is observed and/or measured only indirectly through effects on matter that acquires, loses or possesses it and it comes in many forms such as mechanical, chemical, electrical, radiation (light), and thermal.

The present application focuses on thermal and chemical energy. Thermal energy is the sum of all of the microscopic scale randomized kinetic energy within a body, which is mostly kinetic energy. Chemical energy is the energy of electrons in the force field created by two or more nuclei; mostly potential energy.

Energy is transferred by the process of heat. Heat is a process in which thermal energy enters or leaves a body as the result of a temperature difference. Heat is therefore the transfer of energy due to a difference in temperature; heat is a process and only exists when it is flowing. When there is a temperature difference between two objects or two areas within the same object, heat transfer occurs. Heat energy transfers from the warmer areas to the cooler areas until thermal equilibrium is reached. This is the Second Law of Thermodynamics. There are four modes of heat transfer: evaporation, radiation, conduction and convection.

Molecules are the workhorses and are both vehicles for storing and transporting energy and the means of converting it from one form to another. When the formation, breaking, or rearrangement of the chemical bonds within the molecules is accompanied by the uptake or release of energy it is usually in the form of heat. Work is completely convertible to heat and defined as a transfer due to a difference in temperature, however work is the transfer of energy by any process other than heat. In other words, performance of work involves a transformation of energy.

Temperature measures the average randomized motion of molecules (kinetic energy) in a body. Temperature is an intensive property by which thermal energy manifests itself. It is measured by observing its effect on some temperature dependent variable on matter (i.e. ice/steam points of water). Scales are needed to express temperature numerically and are marked off in uniform increments (degrees).

As a body loses or gains heat, its temperature changes in direct proportion to the amount of thermal energy transferred from a high temperature object to a lower temperature object. Skin temperature rises and falls with the temperature of the surroundings. This is the temperature that is referred to in reference to the skins ability to lose heat its surroundings.

The temperature of the deep tissues of the body (core temperatures) remains constant (within ±1° F./±0.6° C.) unless the person develops a febrile illness. No single temperature can be considered normal. Temperature measurements on people who had no illness have shown a range of normal temperatures. The average core temperature is generally considered to be between 98.0° F. and 98.6° F. measured orally or 99.0° F. and 99.6° F. measured rectally. The body can temporarily tolerate a temperature as high as 101° F. to 104° F. (38.6° C. to 40° C.) and as low as 96° F. (35.5° C.) or lower.

Metabolism simply means all of the chemical reactions in all of the cells of the body. Metabolism creates thermal energy. The metabolic rate is expressed in terms to the rate of heat release during the chemical reactions. Essentially all the energy expended by the body is eventually converted into heat.

Since heat flows from hot to cold temperature and the body needs to maintain a core temperature of 37.0° C.±0.75° C., the heat is conserved or dissipated to the surroundings. The core heat is moved to the skin surface by blood flow. Decreased flow to the skin surface helps conserve heat, while increased flow promotes dissipation. Conduction of the core heat to the skin surface is fast, but inadequate alone to maintain the core temperature. Heat dissipation from the skin surface (3 mm microclimate) also occurs due to the conduction, convection and evaporation.

Heat production is the principal by-product of metabolism. The rate of heat production is called the metabolic rate of the body. The important factors that affect the metabolic rate are:
1. Basal Rate of Metabolism (ROM) of all cells of the body.
2. Extra ROM caused by muscle activity including shivering.

3. Extra ROM caused by the effect of thyroxine and other hormones to a less extent (i.e.: growth hormone, testosterone).
4. Extra ROM caused by the effect of epinephrine, norepinephrine, and sympathetic stimulation on the cells.
5. Extra ROM caused by increased chemical activity in the cells themselves, especially when the cell temperature increases.

Most of the heat produced in the body is generated in the deep organs (liver, brain, heart and the skeletal muscles during exercise). The heat is then transferred to the skin where the heat is lost to the air and other structures. The rate that heat is lost is determined by how fast heat can be conducted from where it is produced in the body core to the skin.

The skin, subcutaneous tissues and especially adipose tissue are the heat insulators for the body. The adipose tissue is important since it conducts heat only 33% as effective as other tissue and specifically 52% as effective as muscle. Conduction rate of heat in human tissue is 18 kcal/cm/m2 k. The subcutaneous tissue insulator system allows the core temperature to be maintained yet allowing the temperature of the skin to approach the temperature of the surroundings.

Blood flows to the skin from the body core in the following manner. Blood vessels penetrate the adipose tissue and enter a vascular network immediately below the skin. This is where the venous plexus comes into play. The venous plexus is especially important because it is supplied by inflow from the skin capillaries and in certain exposed areas of the body (hands-feet-ears) by the highly muscular arterio-venous anastomosis. Blood flow can vary in the venous plexus from barely above zero to 30% of the total cardiac output. There is an approximate eightfold increase in heat conductance between the fully vasoconstricted state and the fully vasodilated state. The skin is an effective controlled heat radiator system and the controlled flow of blood to the skin is the body's most effective mechanism of heat transfer from the core to the surface.

Heat exchange is based on the scientific principle that heat flows from warmer to cooler temperatures. Temperature is thought of as heat intensity of an object. The methods of heat exchange are: radiation (60%), loss of heat in the form of LIR waves (thermal energy), conduction to a solid object (3%), transfer of heat between objects in direct contact and loss of heat by conduction to air (15%) caused by the transfer of heat, caused by the kinetic energy of molecular motion. Much of this motion can be transferred to the air if it is cooler than the surface. This process is self-limited unless the air moves away from the body. If that happens, there is a loss of heat by convection. Convection is caused by air currents. A small amount of convection always occurs due to warmer air rising. The process of convection is enhanced by any process that moves air more rapidly across the body surface (forced convection). This includes fans, air flow beds and air warming blankets.

Convection can also be caused by a loss of heat by evaporation which is a necessary mechanism at very high air temperatures. Heat (thermal energy) can be lost by radiation and conduction to the surroundings as long as the skin is hotter than the surroundings. When the surrounding temperature is higher than the skin temperature, the body gains heat by both radiation and conduction. Under these hot surrounding conditions the only way the body can release heat is by evaporation. Evaporation occurs when the water molecule absorbs enough heat to change to gas. Due to the fact water molecules absorb a large amount of heat in order to change into a gas, large amounts of body heat can be removed from the body.

Insensible heat loss dissipates the body's heat and is not subject to body temperature control (water loss through the lungs, mouth and skin). This accounts for 10% heat loss produced by the body's basal heat production. Sensible heat loss by evaporation occurs when the body temperature rises and sweating occurs. Sweating increases the amount of water to the skins surface for vaporization. Sensible heat loss can exceed insensible heat loss by 30 times. The sweating is caused by electrical or excess heat stimulation of the anterior hypothalamus pre-optic area.

The role of the hypothalamus (anterior pre-optic area) in the regulation of the body's temperatures occurs due to nervous feedback mechanisms that determine when the body temperature is either too hot or too cold.

The role of temperature receptors in the skin and deep body tissues relate to cold and warm sensors in the skin. Cold sensors outnumber warm sensors 10 to 1. The deep tissue receptors occur mainly in the spinal cord, abdominal viscera and both in and around the great veins. The deep receptors mainly detect cold rather than warmth. These receptors function to prevent low body temperature. These receptors contribute to body thermoregulation through the bilateral posterior hypothalamus area. This is where the signals from the pre-optic area and the skin and deep tissue sensors are combined to control the heat producing and heat conserving reactions of the body.

Temperature Decreasing Mechanisms:
1. Vasodilation of all blood vessels, but with intense dilation of skin blood vessels that can increase the rate of heat transfer to the skin eight fold.
2. Sweating can remove 10 times the basal rate of body heat with an additional 1° C. increase in body temperature.
3. Decrease in heat production by inhibiting shivering and chemical thermogenesis.

Temperature Increasing Mechanisms:
1. Skin vasoconstriction throughout the body.
2. Increase in heat production by increasing metabolic activity.
   a. Shivering
      i. 4 to 5 times increase
   b. Chemical Thermogenesis (brown fat)
      i. Adults 10-15% increase
      ii. Infants 100% increase LIR thermography evaluates the infra-red thermal intensity. The microbolometer is a 320×240 pixel array sensor that can acquire the long-wave infrared wavelength (7-14 micron) (NOT near-infrared thermography) and convert the thermal intensity into electrical resistance. The resistance is measured and processed into digital values between 1-254. A digital value represents the long-wave infrared thermal intensity for each of the 76,800 pixels. A grayscale tone is then assigned to the 1-254 thermal intensity digital values. This allows a grayscale image to be developed.

Using LIR thermography is a beneficial device to monitor metabolism and blood flow in a non-invasive test that can be performed bedside with minimal patient and ambient surrounding preparation. The ability to accurately measure the LIR thermal intensity of the human body is made possible because of the skins emissivity (0.98± is 0.01), which is independent of pigmentation, absorptivity (0.98±0.01) reflectivity (0.02) and transmitability (0.000). The human skin mimics the "BlackBody" radiation concept. A perfect blackbody only exists in theory and is an object that absorbs and reemits all of its energy. Human skin is nearly a perfect blackbody as it has an emissivity of 0.98, regardless of actual skin color. These same properties allow temperature degrees to be assigned to the pixel digital value. This is accomplished by calibration utilizing a "BlackBody" simulator and an algorithm to account for the above factors plus ambient temperatures. A multi-color palate can be developed by clustering pixel values. There are no industry standards how this should be done so many color presentations are being used by various manufacturers. The use of gray tone values is standardized, consistent and reproducible. Black is considered cold and white is considered hot by the industry.

An LIR camera has the ability to detect and display the LIR wavelength in the electromagnetic spectrum. The basis for infrared imaging technology is that any object whose temperature is above 0° K radiates infrared energy. Even very cold objects radiate some infrared energy. Even though the object might be absorbing thermal energy to warm itself, it will still emit some infrared energy that is detectable by sensors. The amount of radiated energy is a function of the object's temperature and its relative efficiency of thermal radiation, known as emissivity.

Emissivity is a measure of a surface's efficiency in transferring infrared energy. It is the ratio of thermal energy emitted by a surface to the energy emitted by a perfect blackbody at the same temperature.

LIR thermography is a beneficial device to monitor metabolism and blood flow in a non-invasive test that can be performed bedside with minimal patient and ambient surrounding preparation. It uses the scientific principles of energy, heat, temperature and metabolism. Through measurement and interpretation of thermal energy, it produces images that will assist clinicians to make a significant impact on wound care (prevention, early intervention and treatment) through detection.

In the method of grayscale digital thermographic imaging of abnormalities of the skin and its subcutaneous tissue, the improvement comprising: means for increasing and decreasing pixel value brightness by adding a positive or negative offset to the raw pixel value.

One embodiment of the present invention is in the method of grayscale digital thermographic imaging of abnormalities of the skin and its subcutaneous tissues, the improvement comprising methods and apparatus for defining pixel intensity variations of a long-wave infrared image by measuring the thermal intensity ratio of the average of all pixel values from a skin abnormality region to the average of all pixel values from unaffected skin regions.

Another embodiment of the present invention is in the method of grayscale digital thermographic imaging of abnormalities of the skin and its subcutaneous tissues, the improvement comprising methods and apparatus for maintaining the separation of a thermographic imager from skin at a set distance by converging two light beams emanating from the imager at a point that is the set distance for the imager to be from skin.

Another embodiment of the present invention is in the method of grayscale digital thermographic imaging of abnormalities of the skin at its subcutaneous tissues, the improvement comprising methods and apparatus for obtaining the linear length and width measurements of abnormalities and their square area.

Another embodiment of the present invention is in the method of grayscale digital thermographic imaging of the skin and its subcutaneous tissues, the improvement comprising methods and apparatus for highlighting the digital thermographic image of an area of skin to be measured and calculating the area of the highlighted portion of the image in square centimeters by determining the total number of pixels highlighted.

Another embodiment of the present invention is in the method of grayscale digital thermographic imaging of the skin and its subcutaneous tissues, the improvement comprising methods and apparatus for encircling an area of interest and generating a histogram of the encircled area to project the distribution of pixel values therein.

Another embodiment of the present invention is in the method of grayscale digital thermographic imaging of the skin and its subcutaneous tissues, the improvement comprising methods and apparatus for plotting profile lines in or through an area of skin that is of interest and comparing it with a corresponding profile line of normal skin.

BRIEF DESCRIPTION OF THE DRAWINGS

FIG. 1. Medical long-wave infrared (LIR) and visual views compared.

FIG. 2.1 Effect of adding a positive offset on the thermal span.

FIG. 2.2 Effect of adding a negative offset on the thermal span.

FIG. 2.3 Thermal image of a hand taken with default settings.

FIG. 2.4 Thermal image of the hand when a positive offset is added.

FIG. 13.1 Wound histograms.

FIG. 13.2 Normal histograms.

FIG. 15.1 Comparing the Profile Line with the Reference Line.

FIG. 15.2 Thermal Profile Line.

DETAILED DESCRIPTION OF THE INVENTION

Figure 2:
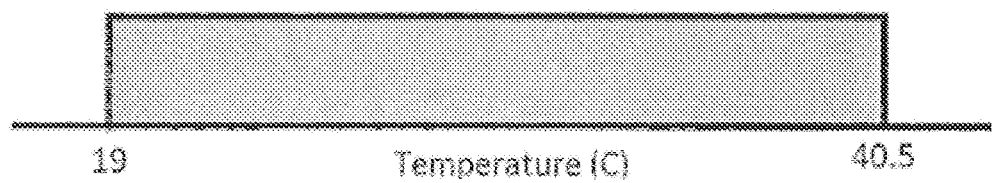
FIG. 2. Thermal span with default configuration settings.

Thermal images taken of the skin surface are constructed by passively reading emitted radiant energy formed by the subcutaneous tissue and the skin tissue by detecting wavelengths in the long-wave infrared range (LIR) of 7-14 microns, and then in real time converting these values into pixels within a digital image. The value assigned to the pixel indicates the thermal intensities of a particular area of the skin when imaged. The thermal images in this embodiment are presented in digital unsigned (not having a plus or minus sign) 8-bit grayscale with pixel values ranging from 0-254, however these same techniques work with images of varying color resolutions. These images could be stored in the data bank along with the information about the data the image has captured so that it can be retrieved by a clinician for future review and analysis. Generally, the unaffected skin thermal intensity will be a uniform gray color within a range of +/−3 to 6 pixel values, which is equal to 0.25 to 0.5 degrees centigrade. Abnormally hot areas of the skin will be represented by patches of increasingly white pixels, while abnormally cold areas will be represented by increasingly dark patches of pixels.

The use of LIR (7-14 microns) imaging along with visual digital imaging allows both physiologic (long-wave infrared and visual) and anatomic assessment of skin and subcutaneous tissue abnormalities and or existing open wounds. The gradiency of the thermal intensity, not the absolute amount of intensity, is the important component of the long-wave thermal image analysis that will allow the clinician to evaluate pathophysiologic events. This capability is beneficial to the clinician in the prevention, early intervention and treatment assessments of a developing existing condition caused by, but not exclusively, wounds, infection, trauma, ischemic events and autoimmune activity.

Utilizing temperature values (F.°, C.°, and Kelvin) as the numerical values of LIR thermal heat intensity is complicated due to the need to have a controlled environment. This is required since the value of the temperature scales is affected by ambient temperature, convection of air, and humidity. These variables would need to be measured and documented continuously if temperature values were used. Also the emissivity, absorptivity, reflexivity and transmitability of the skin and subcutaneous tissue can be affected by skin moisture, scabbing, slough and/or eschar formation in an open wound.

To address this problem the imager utilizes the raw data captured by the microbolometer. This data is utilized in determining pixel values relating to the intensity of the thermal energy from the long-wave infrared electromagnetic radiation spectrum being emitted by the human body. The pixel gradient intensities are represented for visualization by the grayscale presentation.

The pixel values in the grayscale thermal images also vary with the varying conditions mentioned above and hence the algorithms proposed in this application use the average pixel value of the unaffected skin region for that patient on the day the image was taken as a reference point for all the calculations.

Combining the above technique with suggested usage of unaffected skin and subcutaneous tissue in the proximity of an abnormality of a skin/subcutaneous tissue location as a real time control helps to minimize the variability and time consuming requirements in utilizing temperature scales.

There is a difference in the LIR thermal intensity regions of the human body. LIR images have a defined pixel intensity range that is based on the specific usage of an LIR image. In the arena of skin and subcutaneous tissue LIR thermal gradiency, the range is within homeostasis requirements to sustain life. The visualization of pixel intensities is accomplished by the use of a standardized 8-bit grayscale. Black defines cold, gray tones define cool and/or warm and white defines hot. When the imager is used for capturing extremely hot or extremely cold regions that fall outside the thermal range of the imager the pixel values reach the saturation point and it becomes extremely difficult for the human eye to differentiate variations in the pixel values.

This situation can be addressed by utilizing a visualization technique that increases the pixel values to create a positive offset to make the image look brighter. In the same manner a negative offset can be used to decrease the pixel values to make the image look darker.

A. Increasing and Decreasing Pixel Value Brightness by Adding a Positive or Negative Offset to the Raw Pixel Value The positive and negative offset can be utilized to assist in visualizing the area of the body being imaged. The usage of the offsets can then be documented as being used at the time the image is initially taken. The default gray tone that represents the actual pixel values is the raw data being stored in the data bank so future analysis can be performed by clinicians at a later time and/or in another location. The default grayscale data is accompanied by documentation of the use of either the positive or negative offset process. This allows for enhanced visualization of black and white extremes in the grayscale image. The goal is to visually enhance the image at either the lower or higher side of the thermal intensity range without altering the original image.

Referring to FIG. 2, the thermal imager could be configured to capture the thermal intensity variation information within a certain range of thermal intensity. Configuration settings were carefully chosen such that they capture all thermal intensity variations between 19° C. (66.2° F.) to 40.5° C. (104.9° F.), which covers most of the human body's physiologic thermal intensity range. When the thermal intensity of an area of interest gets close to 19° C. (66.2° F.), the pixel values in the grayscale thermal image appear darker and reach a low saturation point. When the thermal intensity drops below 19° C. (66.2° F.), the thermal image would still appear dark but would not get any darker as the low saturation point has already been reached. Similarly as the thermal intensity of an area of interest starts increasing, the thermal image starts looking brighter. As the thermal intensity gets close to 40.5° C. (104.9° F.), the thermal image reaches the high saturation point and the pixel values in the grayscale image reach the maximum value. As the thermal intensity goes beyond 40.5° C. (104.9° F.), even though the thermal intensity of the area of interest is increasing, the thermal image would not appear any brighter as the high saturation point has been reached.

Even though the thermographic imager can pick up thermal intensities as low as 19° C. (66.2° F.) the grayscale thermal image for an area of interest at that thermal intensity would appear too dark. The human eye is not able to visualize the variation of the 254 pixel values included in the standardized grayscale. This might cause problems when thermographic images are taken on areas of the human body with decreased microcirculation, (i.e., the fingers, toes, etc.) or areas with cartilage (i.e., the tip of the nose, ear, etc.). These body locations are usually the coldest on the skin surface thermal intensity and would appear darker in the thermal images.

To solve this problem, a novel technique has been developed to increase or decrease the brightness of the pixel values by adding a positive or negative offset to the raw pixel values. The positive or negative offset allows an enhanced visualization of the black or white extremes in a grayscale image. The goal here is to visually enhance the image at either the lower or higher end of the thermal intensity range without altering the original image.

With default configuration settings and at a room thermal intensity of 22.11° C. (71.8° F.), the thermal intensity range picked up by the thermal imager was as illustrated in FIG. 2.

A low saturation grayscale value of 1 was reached at 19° C. (66.2° F.) and the high saturation grayscale value of 254 was reached at 40.5° C. (104.9° F.), giving a thermal span of 21.5 degrees. The maximum resolution is then 0.0846° C. with in the image.

Formula

> Thermal Span (Thermal intensity range picked up by an imager)=(Thermal intensity at which the pixels reach the high saturation value)−(Thermal intensity at which the pixels reach the low saturation value):
>
> Maximum resolution=(High saturation temperature− Low saturation temperature)/Resolution of the gray scale image For an 8-bit grayscale image the resolution is fixed at 254 parts.

Adding a Positive Offset (Example of Use)

When a positive offset +20 was added to all the pixels to make the image look brighter the imager reached the low saturation grayscale value of 21 at 19° C. (66.2° F.). Since a value of +20 is added to all the pixels, the grayscale value can only go as low as 21 instead of 1 as obtained with default settings. This lowest grayscale value was obtained at the same thermal intensity (19° C.) as the low saturation thermal intensity obtained with default settings. This indicates that adding an offset will only increase the pixel value making it look brighter so that small variations in the pixel values could be visually seen. This does not enable the thermal imager to pick up thermal intensities lower than what can be read with default settings.

With positive offset added, the image appears brighter and reaches the high saturation value at a thermal intensity lower than the high saturation thermal intensity obtained with default settings. The imager reached the high saturation thermal intensity at 39° C. (102.2° F.) instead of 40.5° C. (104.9° F.), as obtained with default settings.

FIG. 2.1 shows the thermal intensity range that is detected when a positive offset is added to the default pixel value configuration setting.

The thermal span is reduced to 20 degrees instead of 21.5 degrees as obtained with default settings when a positive offset was added. The maximum resolution increased to 0.0855° C. which gives more definition to the pixels within the image.

Adding a Negative Offset (Example of Use)

Adding a negative offset to the raw signal coming from the imager makes the thermal image look darker, improving the visualization of the hot (bright) areas. When an offset of −20 was added to the original signal the pixel values reached the low saturation value of 1 at 20.5° C. (68.9° F.) instead of 19° C. (66.2° F.). Since the thermal images are saved as unsigned 8-bit grayscale images with pixel values ranging from 1-254, if the values fall outside this range they would be mapped to 1 or 254. So when a negative value is added, pixels with values less than 20 would become negative and were mapped back to 0 so that the pixel values always stay in the range of 1-254. Similarly on the high end the pixel values reached the highest saturation value of 234 at 40.5° C. (104.9° F.). With a negative offset added the highest the pixel values can go up to is 234 instead of 254. This high saturation occurred at the same thermal intensity as obtained with default settings.

FIG. 2.2 shows the effect of adding a negative offset on the thermal intensity range that could be picked up by the thermal imager.

The thermal span is reduced to 19 degrees giving a maximum resolution of 0.0855° C. within the image.

By choosing a suitable offset (positive or negative) value the visualization of an image is enhanced by increasing the resolution within the image. This concept has been implemented and proven by the researched thermal imaging. An offset of 20 was chosen as an example. This could change based on the requirements. FIG. 2.3 below shows a thermal image of a hand taken with default settings. FIG. 2.4 below shows an example of the effect on the thermal image when a positive offset is added to the pixel values at default settings to improve the visualization of the image.

B. Defining Pixel Intensity Variations in the Long-Wave Infrared Image

Figure 3:
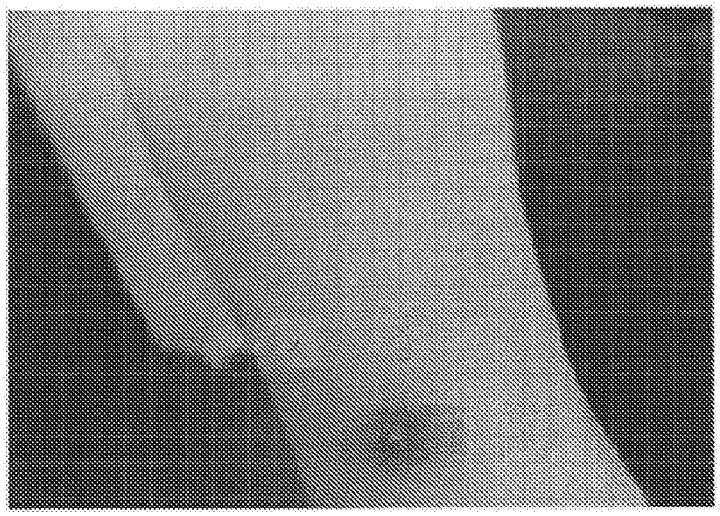
FIG. 3. Normal and abnormal selections made from a thermal image and the corresponding results.
Figure 4:
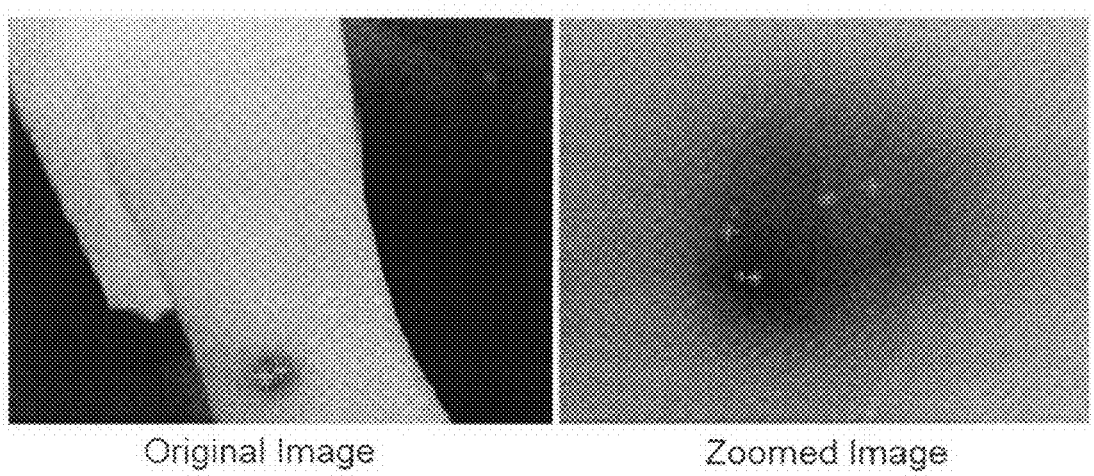
FIG. 4. An original image (left side) and thermal image (right side—zoomed in) with abnormal selections made.

To assist the clinician to define the pixel intensity variations of the long-wave infrared image to see how thermal intensity is varying across the skin area of images taken, as well as previous thermal images of the same location, an inventive technique has been developed that measures the thermal intensity ratio. This gives the clinician the ability to look at the images captured with the thermal imager and choose pixel points in the image utilizing non-zoomed and zoomed presentations of the image that represent skin and subcutaneous tissue surrounding the area of interest. The clinician also has the ability to select the tissue in which an injury/wound exists as shown in FIGS. 3 and 4. The zoomed capability allows the clinician to be very precise in the selection of the pixels used to measure thermal intensity. The zoomed feature is particularly useful because of the complexity of various wound types. For example, the wound base and periwound can be disorganized (acute and chronic condition, etc.), organized (wound resurfacing or repairing, etc.), and/or infected (wound base infection with and without periwound cellulitis, etc.).

FIG. 3 shows a non-zoomed thermal image with unaffected and abnormal selections. The 'X' marks represent the unaffected skin, the asterisk symbol represents the wound base and the circle marks represent the periwound.

FIG. 4 shows an original and zoomed thermal image with abnormal selections. The table in the image shows selected points on the thermal image with their corresponding grayscale values.

Figure 5:
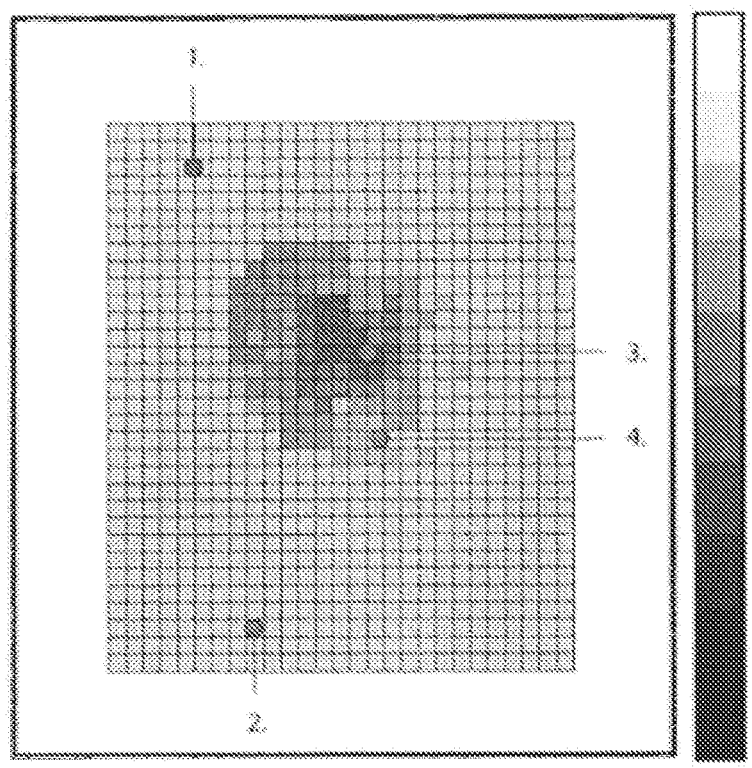
FIG. 5. Schematic representing pixel intensity recognition (zoomed).

FIG. 5 shows a schematic representing pixel intensity recognition (zoomed).

Pixels with uniform gray color represent the unaffected skin and subcutaneous tissue. If the pixel value is too high then it can be an indication of an infection developing in that area. The wound base is usually colder than the unaffected skin's thermal intensity and is represented with darker pixels on a thermal image. The pixel values for a periwound area are usually higher than the wound base pixel value and less than the pixel value associated with the unaffected tissue as their thermal intensity falls between the unaffected skin thermal intensity and the wound base thermal intensity.

The display of pixel value associated with each pixel selection made could help a clinician make a decision on whether an area of interest is present. This allows the following calculations to be performed:

Wound Base to Unaffected Ratio:

> Wound base to unaffected ratio=(Average of all the pixel values from the wound base region)/(Average of all the pixel values from the unaffected region)

Wound base regions are usually colder than the unaffected skin thermal intensity, causing the pixel values for the wound base regions to be lesser than the pixel values for the unaffected skin regions in an LIR image.

If the wound base to unaffected ratio is less than 1, it is an indication that the wound base is colder than the unaffected regional tissue. If the ratio is greater than 1, it is an indication that the wound base area is hotter than the regions selected as unaffected skin area. In summary, the closer the value gets to 1, the closer the wound base area is getting to unaffected skin.

Periwound to Unaffected Ratio:

> Periwound to unaffected ratio=(Average of all the pixel values from the periwound region)/(Average of all the pixel values from the unaffected region)

If the periwound to unaffected ratio is less than 1, it indicates that the periwound is colder than the unaffected skin area. If the ratio is greater than 1, it is an indication that the periwound area is hotter than the regions selected as unaffected skin area. In summary, the closer the value gets to 1, the closer the periwound area is getting to unaffected skin.

Periwound to Wound Base Ratio:

> Periwound to wound base ratio=(Average of all the pixel values from the periwound region)/(Average of all the pixel values from the wound base region)

The ratio greater than 1 indicates that the periwound region is hotter than the wound base region and the ratio less than 1 indicates that the wound base region is hotter than the periwound region. In summary, the closer the ratio gets to 1, the closer the wound base and periwound values get to each other.

By monitoring these ratios the clinician could get a better idea on the status of the wound.

C. Maintaining Separation of the Imager from Target

Long-wave infrared and visual images must be consistently taken at a predetermined distance, typically 18 inches. This capability allows measurements to be obtained by length×width, by linear measurement, and by encirclement of the area of interest and or wound. This information is considered to be the gold standard of the wound care industry in determining the progression or regression of abnormalities.

Thermal and visual cameras are used for capturing images of areas of interest, such as wounds in a real time fashion (i.e., bedside or outpatient clinic). Cameras are built so that they can communicate with computer via a USB connection and capture both visual and thermal images by clicking the trigger button on the camera.

All the images need to be captured at a certain distance from the body part and a standard distance of 18 inches between the camera and the body part was found in testing done to date to be an ideal distance. Several methods were used in order to measure this distance.

As a first attempt an antenna of length 18 inches was placed on the camera core that could be extended out. When the end of the antenna touched the body part the standard distance was known to have been attained, indicating that the camera is ready for capturing images. The adverse effects of using an antenna for measuring the distance were that the antenna would be touching the body part giving rise to possible risk of contamination, and also that the antenna comes into the field of view when the image is being captured causing problems with visualization.

To overcome these problems the antenna method was replaced with a more sophisticated method using ultrasonic sound waves. An ultrasonic transducer placed on the camera core would release ultrasonic sound waves for transmission in the desired path and when these waves hit the target, which would be the body part in our case, and ultra sonic sound waves would be reflected back from the target in the transmission path. The received ultrasonic sound waves can then be converted into an electrical signal that can be processed by a processor to provide distance information. The distance can be computed by using the time period from the middle time value of the received electrical signal to the middle time value of the transmitted signal. Whenever this distance equals the standard distance of 18 inches a reduced audible noise will be generated, indicating that the camera is ready to capture an image.

Even though the ultrasonic sound wave method has been proven to be successful and has been used in various applications to date for measuring the distances, it was never used in the medical field at bedside as a tool for capturing visual and thermal images.

Limitations of using the ultrasonic method included the complexity of wiring and the size of the apparatus used for measuring the distance and then displaying it so that the end user can see how far the camera is from the target. The other major limitation arose with the presence of an object in between the camera and the target. When there is an object in the path, part or all of the waves will be reflected back to the transmitter as an echo and can be detected through the receiver path. It is difficult to make sure that the received ultrasonic sound waves were actually reflected by the target and not by any other object in the path.

The ultrasonic measuring of the distance was replaced with the use of two Class I Laser LED lights. Two Class I A, or of less strength, lasers and/or LED modified lights are used in this method. These lasers emit narrow light beams as opposed to diffused light. They are placed on either side of the camera lens. When the distance between the camera and the target is less than 18 inches the lights coming from these lasers fall on the target as two spots separated by a distance and this distance will keep decreasing as the camera is moved toward from the target. When the distance between the camera and the target equal 18 inches the lights from these two light sources will coincide, indicating that the focus point has been achieved and that the camera is ready for capturing images. The distance between the two light beams starts increasing again when the distance between the camera and the target increases to the standard 18 inches.

Figure 6:
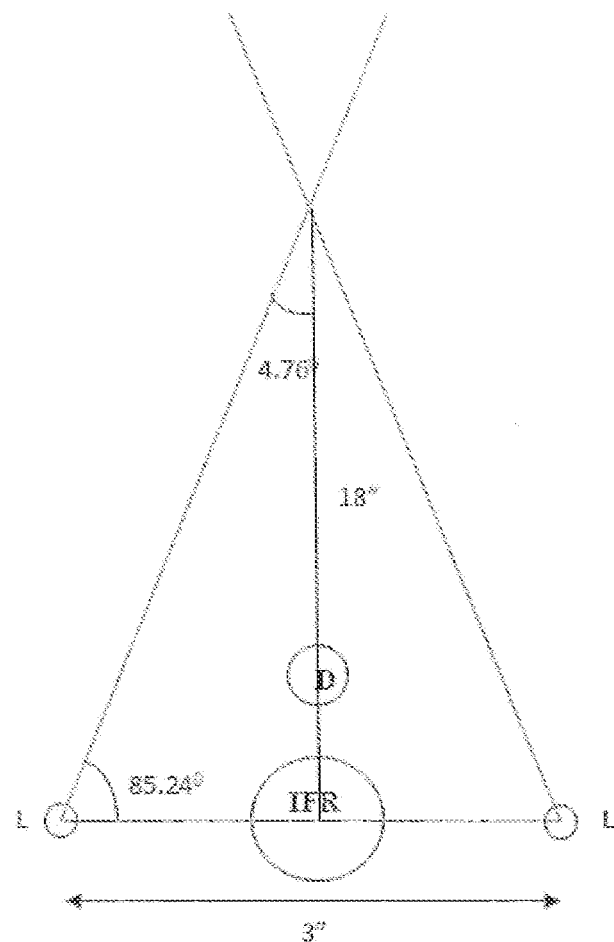
FIG. 6. Diagram of laser lights implementation.

FIG. 6 explains the above embodiment in more detail, where IFR represents the long-wave infrared microbolometer and D represents the visual digital camera, and L represents the laser lights.

Depending on how far the laser lights are going to be from the microbolometer and the distance between the microbolometer and the target the angles at which the lasers need to be inclined will change.

The digital camera 'D' is also going to be placed at around 1.5 inches away from the long-wave infrared microbolometer and in order to make both the digital and the long-wave infrared microbolometer to have the same focus point and field of view the digital camera needs to be inclined at an angle.

Figure 7:
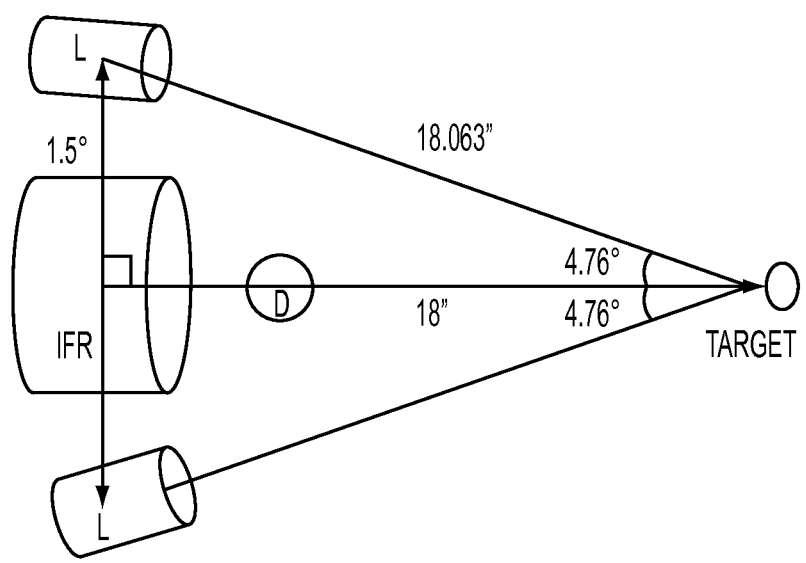
FIG. 7. Experimental setup used to determine digital camera and long-wave infrared microbolometer angels of inclination.

The experimental setup of FIG. 7 that was used in order to determine the angle of inclination is as shown.

Figure 8:
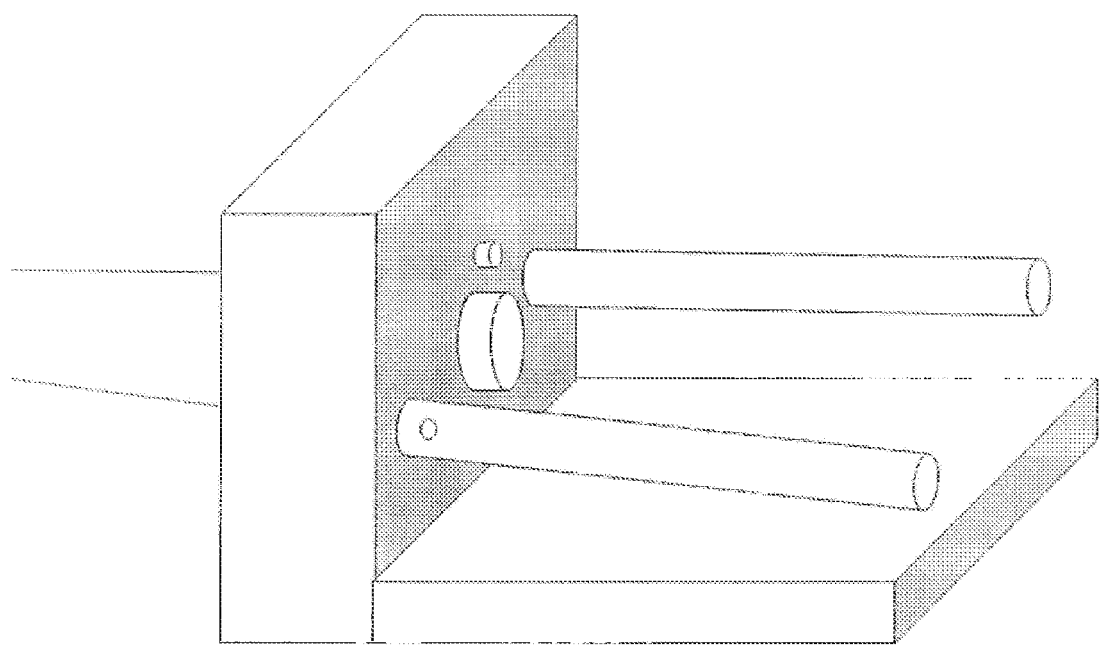
FIG. 8. An embodiment of laser lights at an 18 inch distance.

FIG. 8 is a representation of an embodiment that uses 18 inches as the desired distance in a clinical setting. By changing the angles of the Class 1 Lasers this distance can be increased or decreased to meet other needs or requirements determined by the clinician.

D. A Consistent Technique to Obtain Wound Measurement Length and Width Linearly Using a Thermal Image To assist clinicians with maintaining accuracy and consistency when measuring a wound, a novel technique has also been developed to obtain consistent linear wound measurements (length and width) using a thermal image. It allows a clinician to follow a standard of care to determine the progression and regression of the wound by measuring length and width and area.

To be able to obtain the measurements of a wound from an image the number of pixels available per centimeter or per inch in that image needs to be known. When images are always taken from a standard distance the number of pixels per inch in that image always remain constant, and they change with the change in the separation distance between the imager and the target.

The imager has been designed such that the separation distance between the imager and the target is always maintained at 18 inches. Several techniques like using a measuring tape, using ultrasound and using Class 1 lasers have been tried and tested to date to maintain this standard distance. The final version of the imager makes use of two Class 1 lasers mounted inside the imager at an angle such that the laser beams emitted from these two lasers always converge at 18 inches from the front of the camera.

For an image taken at a distance between the object being imaged and the imager that is exactly 18 inches there would be in the image approximately 40 pixels per inch. This distance can be changed, but at each distance the number of pixels needed to equal 1 cm or 1 inch must be measured and tested. The selected distance must be noted to maintain reproducibility. For the calculation of length and width of the wound, when a line is drawn across the area of interest by measuring the number of pixels covered across this line and using a conversion formula the measurement in pixels could be converted into inches or centimeters. For an image taken at 18 inches from the target, a line that is 40 pixels in length would be approximately 1 inch on the measuring scale and using the inch to centimeter conversion the length could then be converted into centimeters.

Algorithm for Measuring Length and Width of an Area of Interest (in Centimeters)

Draw a line across the image that represents the length or width of the area of interest that needs to be measured.

Note the x and y coordinates of the starting and ending points of this line.

If (x1,y1) represent the x and y coordinates of the starting point of the line and (x2,y2) represent the x and y coordinates of the end point of the line then the distance between these two points (length of the line in pixels) can be measured as:

$$\text{Length (or width) in pixels} = \sqrt{(x2-x1)^2 + (y2-y1)^2}$$

Length (or width) in inches=Length in pixels/40

Length (or width) in centimeters=Length in pixels/15.7480

As per Minimum Data Set (MDS) Version 3.0, it is recommended that the length of a wound is always measured as the longest length drawn from head to toe and width is measured as the widest width drawn side to side perpendicular to the length. The x or y coordinates of the end point of the line representing the length or the width line could be adjusted to make sure the lines are exactly vertical or horizontal which would in turn make them perpendicular to each other.

Using the length and the width measurements (length× width) area could be calculated.

Figure 9:
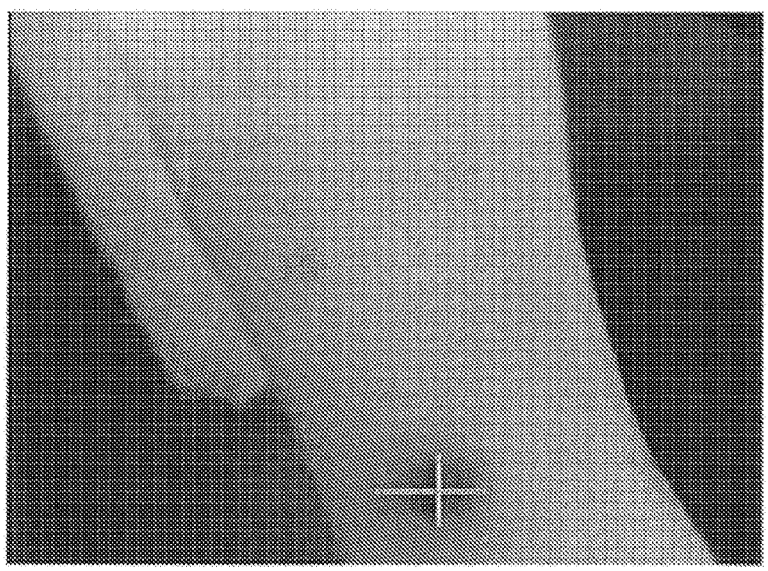
FIG. 9. Length and width measurements form an area of interest.

By monitoring the thermal images taken on day to day basis, and by measuring the length and the width for the area of interest each day, the status of the wound could be monitored to see whether there has been a progression or regression in the status. FIG. 9 shows the length and width measurement in centimeters obtained for an image with an area of interest on a heel.

E. Highlighting the Wound Base, Periwound and Unaffected Regions to Measure and Calculate the Square Areas Thereof by Using the Number of Pixels Highlighted A novel technique has been developed that gives the clinician the ability to highlight a wound base, periwound or unaffected regions and to measure the area in square centimeters. This will assist the clinician in looking at the overall status of the wound, and evaluating its progression or regression.

The total number of pixels enclosed within the highlighted area could be used for calculating the area of the region selected.

A test target of size 1.5 inch×1.5 inch was used. With the imager at 18 inches from the test target, images were captured.

The area of test target=1.5 inch×1.5 inch=2.25 square inches or 3.81 cm×3.81 cm=14.5161 square cm.

For an image taken at 18 inches from the target there would be approximately 40 pixels per inch. So there would be approximately 60 pixels in 1.5 inches.

The area of the test target obtained from the image=60 pixels×60 pixels=3600 pixels. A total of 3600 pixels were enclosed inside the area of the test target.
So 3600 pixels ↔ 14.5161 square cm For an unknown area of interest, if "Y" is the number of pixels enclosed inside that area then the surface area in square centimeters for that region would be equal to:

$$\text{Area in square centimeters for the highlighted region} = (Y \times 14.5161)/3600$$

Figure 10:
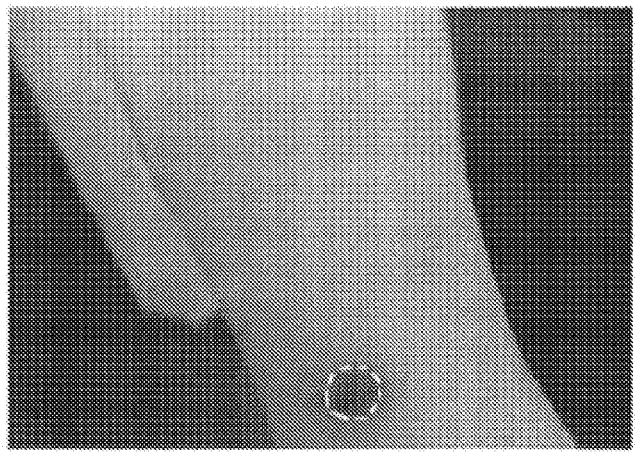
FIG. 10. Schematic representing pixel intensity recognition (zoomed.)

For the region highlighted as the wound base, area in square cm's and average of all the pixel values falling inside the highlighted region are calculated and displayed in the picture as shown in FIG. 10.

Figure 11:
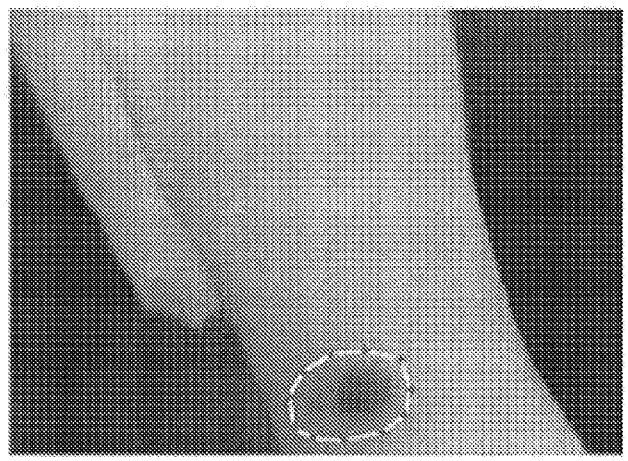
FIG. 11. Periwound region including the wound base highlighted as area of interest and the results obtained for the area selected.

Periwound area represents the area surrounding the wound base. By highlighting the area that includes the wound base and the periwound area surrounding it as shown in FIG. 11, and by counting the number of pixels enclosed in that region, the area of the highlighted region could be calculated in square centimeters. The periwound area could then be obtained by subtracting the wound base area from the area that includes both the periwound and the wound base areas.

By including the unaffected skin and subcutaneous tissue surrounding the wound in the highlighted area of interest, the unaffected area could be calculated in square centimeters. The unaffected area could then be obtained by subtracting the wound base and periwound area from the region selected that includes unaffected, periwound and the wound base areas.

Figure 12:
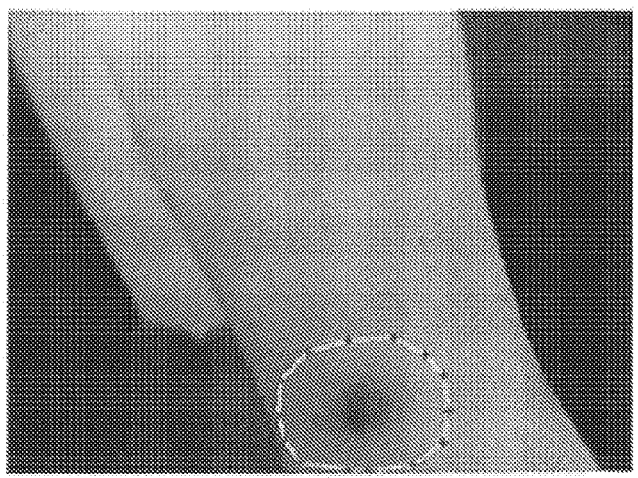
FIG. 12. Area including normal, periwound and the wound base regions highlighted as area of interest and the corresponding results obtained for the area selected.

FIG. 12 below shows the calculations displaying the highlighted unaffected area and the various calculations obtained from the highlighted regions.

F. Obtaining the Average Pixel Value and the Plus/Minus Variance by Encircling the Area of Interest/Wound By utilizing the novel techniques above, not only can the area be calculated, but simultaneously the average pixel value of each area can be calculated. This will allow the clinician to evaluate the status of the area of interest or wound not only in micro (focused technique, above) but also in the macro using the technique described below. The combination of these two assessments will give a better overall understanding of the areas of interest where the abnormality or wound has been identified. From this average data the ratio concept discussed above can also be used to evaluate the macro (overall) look at an area of interest or wound, specifically if the wound is becoming organized, i.e., is it improving, becoming infected, or regressing (getting worse). See Table 1 below.

TABLE 1

Summarizing the results obtained from the highlighted normal, periwound, and wound base regions

|  | Normal | Periwound | Wound Base |
|---|---|---|---|
| Area in sq. cm | 29.03 | 16.66 | 7.71 |
| Average pixel value | 125.17 | 103.82 | 61.09 |
| Minimum and maximum pixel values | [Various range] | [Various range] | [Various range] |

Some of the other measurements that could be done to keep track of the status of an area of interest include calculating the average, minimum and maximum of all the pixel values falling inside the highlighted area.

> Average pixel value=Sum of pixel values for all the pixels that fall inside the highlighted area of interest/Total number of pixels falling inside the highlighted area For a highlighted area of interest a histogram can be generated to provide graphical representation of distribution of pixel values within that area.

Algorithm for Generating Histograms
Highlight the area of interest for which a histogram needs to be generated
Determine the total number of bins/buckets into which the data needs to be divided into. There is no best number of bins, and different bin sizes can reveal different features of the data. Bin size can be calculated as > Bin size=Maximum value−Minimum value/Total number of bins For a thermal image the pixel values always range between 0 and 255
Create an empty array of size equal to the total number of bins
Check to see if a pixel falls inside the highlighted area of interest and if it does note the pixel value
The bin number into which this pixel value falls under can be calculated using the formula > Bin number=Pixel value−Minimum value/Bin Size Increment the value of the array at the index [Bin number−1], since arrays are zero based, by one.
Repeat the steps 5-7 for all the pixels in an image
After checking all the pixels in an image, plot the array to generate a histogram.

Clinical Significance of Histograms

Distribution of pixel values as projected by the histograms for a highlighted area of interest provides more in depth information about the signature of a wound. If the histogram plot is more spread out it indicates there is a large variation in the pixel values and hence temperatures within the highlighted area as shown in FIG. 13. As the plot starts getting more and more narrow it is an indication that all the pixels inside the highlighted portion are getting close to each other and the temperature inside the highlighted portion is starting to get saturated towards a single temperature value. If the saturation occurs at a higher pixel value then it is an indication that all the pixels inside the highlighted portion are getting very hot compared to the selected normal reference point. Similarly if the saturation occurs at a very low pixel value then all the pixels inside the highlighted area are getting very cold. FIG. 13 shows some sample histograms generated for an image with a highlighted area of interest.

G. Creating Profile Lines in and Through an Area of Interest/Wound and Comparing with Profile Lines Trough Reference Areas A novel feature has been developed to assist a trained clinician to better track a wound by utilizing the ability to plot profile lines through the wound. These plots show the variation in the pixel values across the wound. Since the thermal intensity is directly related to the grayscale pixel values in an image, these plots can be used to monitor how the thermal intensity is varying across an area of interest or wound. This allows the clinician to dissect the wound in precise fashion so the pathophysiologic status of the wound can be assessed and quantified.

Figure 14:
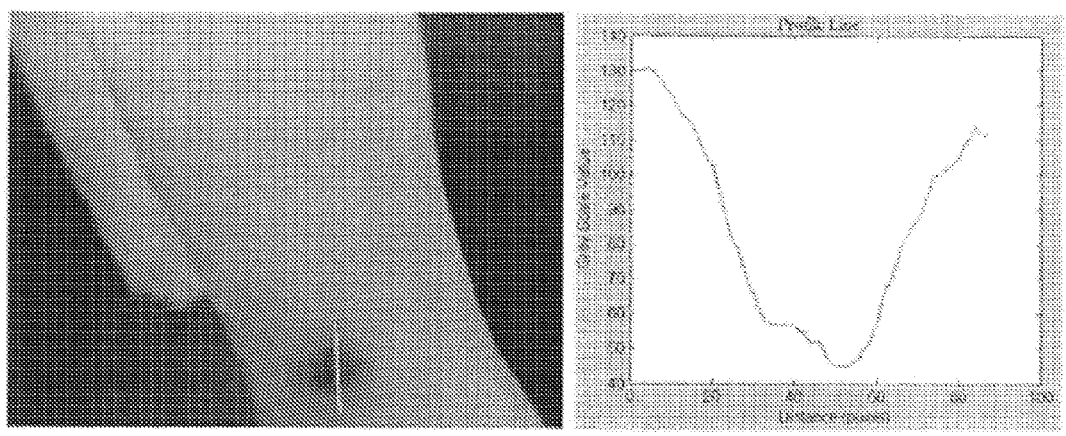
FIG. 14. Profile line showing the variation in the grayscale values along the line drawn over an area of interest.

Profile lines can be plotted by simply drawing a line across the area of interest. FIG. 14 below shows an example of the profile line generated by drawing a line across the wound present on the heel. As seen in the plot there is a huge drop in the pixel value/thermal intensity across the wound base region and the value starts increasing as the line is moving away from the wound base and entering areas with unaffected skin tissue.

As the wound starts healing the difference between the pixel value for the unaffected tissue and the pixel value from the wound base starts decreasing and hence the drop seen in the graph starts decreasing indicating that the wound is healing and is starting to get close to the unaffected skin tissue.

If the drop in the pixel values starts increasing, when plots are generated for images taken on timely basis then it is an indication that the wound is deteriorating and that the clinician needs to turn to strategies to facilitate wound healing.

Algorithm for Generating the Profile Lines
Draw a line across the area of interest for which the profile lines need to be plotted.
Record the X and Y locations of the starting and end points of the profile line. Let (x1, y1) represent the coordinates of the starting point and (x2, y2) represent the coordinates of the end point.
deltaX=absolute value of (x2−x1); deltaY=absolute value of (y2−y1)
length of the line=$L=\sqrt{(x2-x1)^2+(y2-y1)^2}$
x_increment=deltaX/L
y_increment=deltaY/L
Round off L to the nearest integer and then increment by 1; L=L+1

Create a new array to hold the pixel values that fall across the profile line. Let us call this array 'Pixel values'.
Pixel_values(1)=pixel value of the image at the location x1, y1
Add the x_increment and y_increment to the original x1 and y1 respectively and use these as new values for x1 and y1
So x1=round (x1+x_increment)
 y1=round (y1+y_increment)
Create a new counter variable, let us call it 'i'
i=1;
While ((i<L) && (x1, y1 fall within the size of the image)
  Pixel_values (i+1)=pixel value of the image at the location x1, y1;
  x1=round (x1+x_increment);
  y1=round (y1+y_increment);
  i=i+1;
End
The array 'Pixel_values' should contain values of all the pixels that represent the profile line Plotting the values in the array 'Pixel_values' gives the plot for the profile line drawn across the area of interest (as shown in the figure above).

Images taken using a thermal imaging camera can be analyzed and tracked to monitor the status of wounds.

Profile lines provide a tool for monitoring variations in pixel values and hence the temperatures across the abnormal areas of interest. These variations can be compared against the pixel value representing unaffected region for that patient by selecting a region on the image that represents unaffected skin.

Comparing the Profile Line with the Reference Line Representing the Unaffected Skin for that Patient Comparing the pixel values of the pixels falling across the profile line with the reference pixel value that represents unaffected skin for that patient gives a measure of how close or far away the profile line pixel values are from the selected reference line.

For selecting unaffected regions a circle can be drawn on the image that comprises of only the unaffected pixels and does not include any abnormalities or the background. Once a circle has been drawn representing unaffected skin for the patient, average of all the pixels falling inside the circle can be calculated as follows:

Average Normal pixel value=Sum of all the pixels that fall inside the circle representing Normal/Total number of pixels inside the circle To determine whether a pixel falls inside a circle of radius 'r' calculate the distance between the center of the circle and the coordinates of the pixel point using the formula $$Distance = \sqrt{(x2-x1)^2 + (y2-y1)^2}$$

where (x1, y1) represent the X and Y coordinates of the center of the circle and
  (x2,y2) represent the X and Y coordinates of the pixel
If the distance is less than the radius of the circle then that pixel falls inside the circle representing unaffected skin area.

Once the average normal pixel value has been calculated this value can be plotted on the chart along with the profile line as shown in the FIGS. 15.1 and 15.2.

By comparing the profile line with the normal line the status of the area of interest can be tracked. As the profile line gets closer to the reference line it indicates that the area of interest is improving and is getting closer to the normal skin characteristics.

The portions below the reference line represent the segments of the profile line where the pixel values are lower (colder) than the selected normal reference point. Similarly the points falling above the reference line represent the portion of the profile that is hotter than the selected normal reference.

Once a normal reference point has been chosen and a profile line has been drawn several parameters can be calculated to compare the profile line signature with the reference line signature. By tracking how these values change on day to day basis the status of the wound could be tracked.

Some of the factors that could be calculated to compare the profile line with the reference line include area above and below the reference line, maximum rise and drop, average rise and drop from the reference line etc.

The area calculations also give a measure of the portion of the profile line that falls above or below the normal reference line. The area that falls above the reference line indicates the regions that have a pixel value higher that the reference point and hence are at a higher temperature. The area below the reference line shows the portion of the profile line that has temperatures lower than the selected reference.

The areas can be calculated using the Trapezoidal rule of calculating area under the curve.

Calculating Area Above and Below the Reference Line

Figure 16:
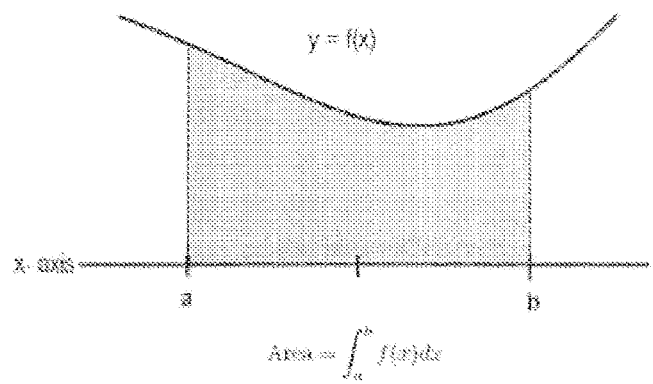
FIG. 16. Figure illustrating the formula for calculating area under the curve.

The area between the graph of y=f(x) and the x-axis is given by the definite integral in FIG. 16 (Reference: http://www.mathwords.com/a/area_under_a_curve.htm). This formula gives a positive result for a graph above the x-axis, and a negative result for a graph below the x-axis.

Note: If the graph of y=f(x) is partly above and partly below the x-axis, the formula given below generates the net area. That is, the area above the axis minus the area below the axis.

The trapezoidal rule (also known as the trapezoid rule or trapezium rule) is an approximate technique for calculating the definite integral as follows $$\int_a^b f(x)dx \cong \frac{\Delta x}{2} * (f(x0) + f(xn) + 2*(f(x1) + f(x2) + \ldots + f(x(n-1))))$$

Where $\Delta x=(b-a)/n$, $x0=a$, $x1=a+\Delta x$, $x2=a+2\Delta x$ ... $xn=a+n\Delta x=b$ and 'n' is the number of equal length subintervals into which the region [a, b] is divided into.

To calculate area relative to the Normal line, instead of x-axis, pixel values relative to the selected normal need to be calculated which equal to the actual pixel value–the selected normal value.

Figure 17:
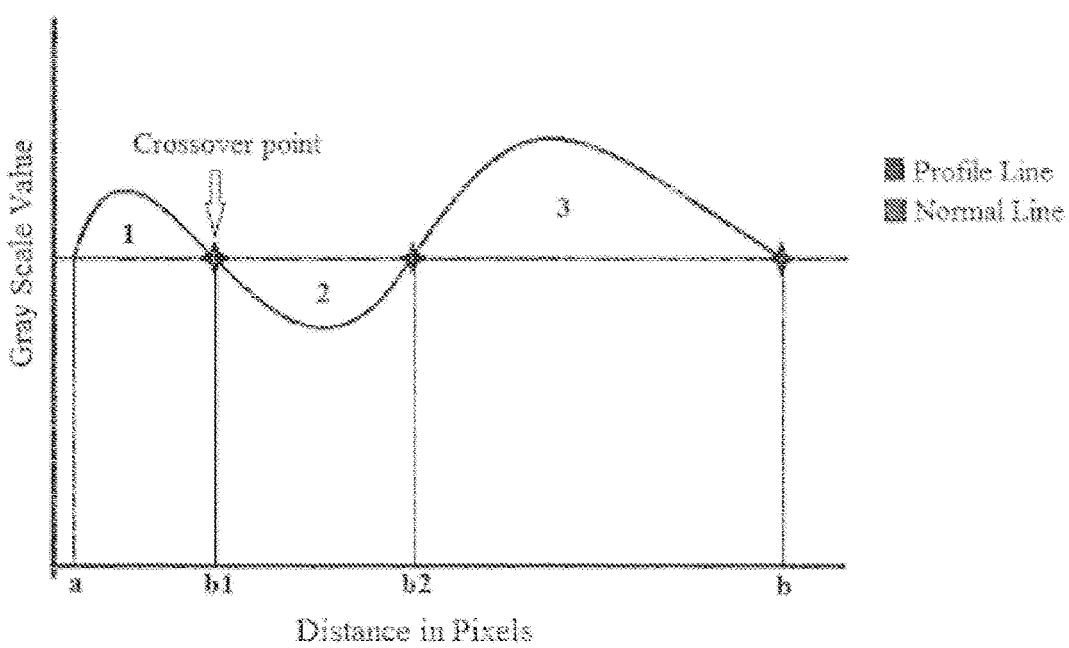
FIG. 17. Calculating areas above and below the selected normal.

If relative pixel value is positive it indicates that the point falls above the normal line and if negative it falls below the normal line. Whenever the relative pixel value across the curve goes from positive to negative or vice versa it is an indication that there has been a crossover across the normal line. The algorithm for computing the area above and below the normal line can be summarized as follows:
Calculate relative pixel values
Find out where the crossover points occur
Split the curve into positive and negative regions
Calculate area for each region separately using the Trapezoidal rule
Finally, combine all positive areas to obtain area above normal line and all the negative areas to obtain the area below the normal line FIG. 17 shows a plot of a sample profile line and a normal line. As shown in the figure the sample profile lines crosses the normal line at three points dividing the curve into three regions. Regions 1 and 3 fall above the normal line and have positive relative pixel values whereas the region 2 falls below the normal line and has negative relative pixel values.

To calculate the area above and below the normal for the sample plot the area for the three regions need to be calculated individually using the Trapezoidal rule.

Area for the region 1=

$$\int_a^{b1} f1(x) \cong$$

$$\frac{\Delta x}{2} * (f1(a) + f1(b1) + 2*(f1(x1) + f1(x2) + \ldots + f1(x(n-1))))$$

Where f1(x) defines the curve in region 1
$\Delta x = (b1-a)/n$, $x1 = a+\Delta x$, $x2 = a+2\Delta x \ldots xn = a+n\Delta x = b1$ and 'n' is the number of equal length subintervals into which the region [a, b1] is divided into.

Area for region 2=

$$\int_{b1}^{b2} f2(x) \cong$$

$$\frac{\Delta x}{2} * (f2(b1) + f2(b2) + 2*(f2(x1) + f2(x2) + \ldots + f2(x(n-1))))$$

Where f2(x) defines the curve in region 2
$\Delta x = (b2-b1)/n$, $x1 = b1+\Delta x$, $x2 = b1+2\Delta x \ldots xn = b1+n\Delta x = b2$ and 'n' is the number of equal length subintervals into which the region [b1, b2] is divided into.
Similarly area for region $3 = \int_{b2}^{b} f3(x)$ where f3(x) defines the curve in region 3
The area for this region would be negative indicating that it falls below the normal line.
Area above the Normal line can be obtained by adding areas under regions 1 and $3 = \int_a^{b1} f1(x) + \int_{b2}^{b} f3(x)$
Area below the Normal line=Area under the region $2 = \int_{b1}^{b2} f2(x)$ By counting exactly how many number of pixels fall above or below the reference line the percentage of profile line that falls above or below the profile line can be calculated as follows:

Percentage of profile line that falls above the reference line=(Number of pixels that fall above the reference line)*100/Total number of pixels across the profile line Percentage of profile line that falls below the reference line=(Number of pixels that fall below the reference line)*100/Total number of pixels across the profile line Percentage of profile line that falls along the reference line=(Number of pixels that fall on the reference line)*100/Total number of pixels across the profile line Maximum rise above the reference line gives the maximum positive difference in the pixel values between the profile line and the reference line. A rise in this value indicates that the temperature for some of the pixels along the profile line is getting much hotter than the reference value and decrease in this value indicates that the maximum difference between the profile line pixel values and the reference line pixel values is decreasing and that the profile line is getting closer to the reference line.

Similarly Maximum drop below the reference line can be calculated as the maximum negative difference in the pixel values between the profile line and the reference line. An increase in the maximum drop indicates that the pixels on the profile line are colder than the average reference pixel value.

Average rise and average drop can also be used as factors for comparing the profile lines with the reference line. Formulae for calculating average rise and average drop are as follows:

Average rise above the reference line=Sum of all the pixels that fall above the reference line/Total number of pixels that fall above the reference line Average fall below the reference line=Sum of all the pixels that fall below the reference line/Total number of pixels that fall below the reference line Slopes: Calculating slopes for the profile lines gives information about how often the temperature varies along the profile line. A slope line can be drawn on the profile line every time there has been a significant change in the pixel value (temperature). A positive slope indicates an increase in temperature and a negative slope indicates a drop in the temperature. The steepness of the slope lines indicates the amount of variation in temperatures. The steeper the lines the larger the variation is temperatures and the more irregular the profile line is.

An algorithm for calculating slopes and generating slope lines across the profile line can be summarized as follows:
Select a suitable value for slope variance, a value which indicates how much of a difference in pixel values between two points on the profile line is considered as a signification change.
Consider the starting point of the profile line as the starting point of the first slope line. Starting from this point and by moving along the profile line calculate the difference between the current pixel value and the pixel value at the starting location. If the difference is greater than or equal to the slope variance, the point at which the difference exceeds the slope variance becomes the end point for the slope line.
Draw a line on the profile line joining these two points.
Slope for this line can be calculated as follows:
If (x1, y1) represents the x and y coordinates of the starting point and (x2, y2) represent the coordinates of the end point of the slope line then the slope for this line can be calculated as Slope=$(y2-y1)/(x2-x1)$ Save this slope value in an array.
Make the end point of the first slope line as the start point for the next slope line to be generated and repeat step 2 to determine the new end point.
Once the start and end points of the slope lines is established plot the slope line on to the profile line and then calculate and save the slope values.
Repeat the process until the end of profile line is reached
FIG. 15.2 shows a slope line plotted on to the profile line with a slope variance of 12.

These are some of the factors that can be calculated from the profile line and reference line plots that help define the signature of the area of interest.

All the activity done by the clinician on the images can be recorded and saved in a database. The information can be retrieved on a later date to see which regions were selected as area of interest on that particular day, and to see what changes have occurred and how the results have changed with time. This novel approach will enable a trained clinician to better evaluate the area of interest/wound of the skin and subcutaneous tissue in a standardized and reproducible format.

The benefits related to using this advancement in long-wave infrared thermal imaging spans improvement in potential care, fulfilling regulatory requirements and fiduciary responsibility by reproducible and standardized documentation and cost savings secondary to the ability of clinicians to formulate appropriate individualized care plans for prevention, early intervention and treatment of abnormalities of the skin and subcutaneous tissue.

H. Using the Profile Line Plot to Interpret Wounds

Once a profile line is drawn on the image across the area of interest a profile line plot can be generated using the algorithm outlined above. The plot can then be used to determine where on the profile line a drop or rise in the pixel value (temperature) occurs. The profile line plot can be made interactive so that when the user clicks on the plot the corresponding location on the image can be highlighted and hence making it easier to interpret. The algorithm for implementing this can be briefly summarized as follows:
1. Generate an interactive plot for profile line using tools like Telerik
2. Create a chart item click event for the plot so that when the user clicks on the profile line plot the x and y values of the click point are recorded
3. The X axis value at the click point (saved as 'index') shows how far away the point falls from the start point of the profile line. The Y value gives the actual pixel value at the point.
4. To locate this point on the profile line drawn on the image, the actual X and Y coordinates on the image need to be determined. The X and Y coordinates of the click point can be obtained as follows:
5. Calculate the length of the profile line using the start and end coordinates of the profile line.
6. If (X1,Y1) represents the coordinates of the starting point of the profile line on the image and (X2,Y2) represent the end point then the length can be calculated as
7. length of the line=$L=\sqrt{(X2-X1)^2+(Y2-Y1)^2}$
8. deltaX=absolute value of (X2−X1); deltaY=absolute value of (Y2−Y1)
9. x_increment=deltaX/L; y_increment=deltaY/L
10. if (x_increment>0 && y_increment<0)
    {
       index=L−index:
    }
11. The X and Y coordinates of the point that represents the click point can then be obtained as
    X=X1+(index*x_increment);  Y=Y1+(index*y_increment);
12. Draw a string on the image at the X and Y coordinates from the previous step to indicate the click point Similar technique can be used to determine where a point on the image falls on the profile line. The algorithm for doing this can be outlined as follows:
1. Add a Mouse down click event for the image.
2. Note the X and Y coordinates of the point where the user clicked on the image.
3. Check whether this point falls on the profile line
4. If the point falls on the profile line calculate the distance between the start point of the profile line and the point where the user clicked.
5. This distance indicates how far the point falls on the plot from the start point of the graph.
6. Draw on the graph to indicate this point.

Figure 18:
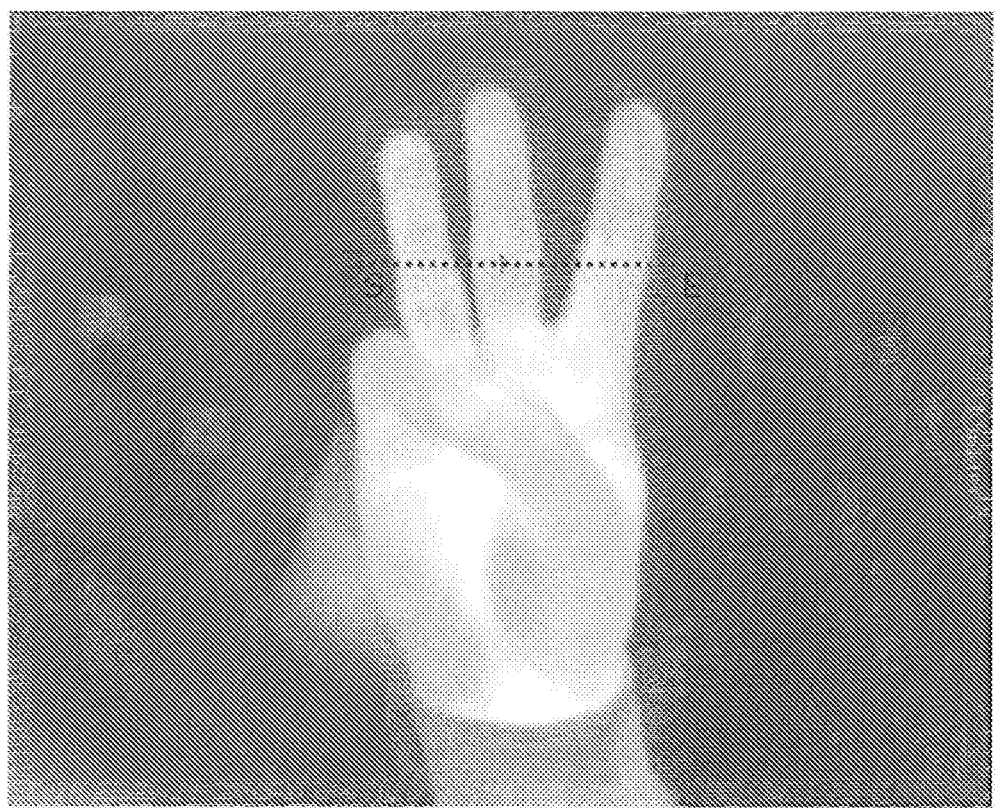
FIG. 18. Profile Line drawn through three fingers.
Figure 19:
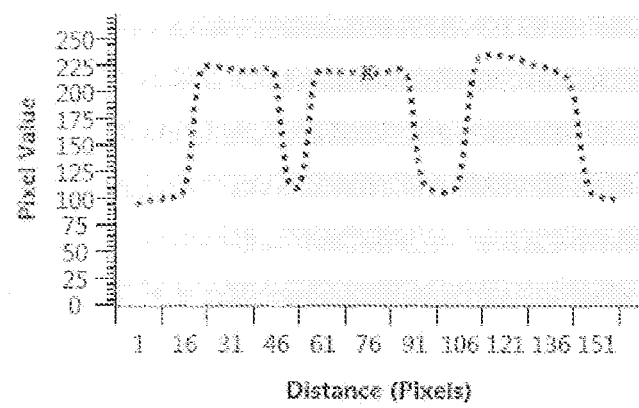
FIG. 19. A Profile Line plot on a graph.

FIG. 18 shows a profile line drawn on the image of a hand and FIG. 19 shows the profile line plot. The X mark on the graph and the image indicates the user's selected point.

We claim:

1. A combination thermal and visual image capturing device used to capture real time thermal and visual images of surface and subsurface biological tissue, said device comprising: a power source, said power source functionally connected to said device; a generally pistol shaped housing, a long wave infrared microbolometer, said microbolometer functionally connected to said power source a digital camera, said digital camera functionally connected to said power source and disposed at a collinear position relatively distal from said microbolometer; a first of LED laser, said first laser functionally connected to said power source and at a predetermined distance from said microbolometer; a second LED laser, said second laser functionally connected to said power source and disposed at a predetermined distance from said microbolometer opposite said first laser, wherein each said laser is disposed along a line perpendicular to a line disposed through the central axis of said microbolometer and said digital camera, and where each laser is disposed to emit light at a predetermined angle relative to the image capturing device, said imaging apparatus further comprising means to electronically provide thermal image information from the microbolometer and visual image information from said digital camera to another electronic device or system.

2. The apparatus of claim 1, wherein the another electronic device is a video screen.

3. The apparatus of claim 1, wherein the another electronic device is computer.

4. The apparatus of claim 1, wherein the another electronic system is the Internet.

5. The apparatus of claim 1, wherein the another electronic device is a smart phone.

6. The apparatus of claim 1, wherein the another system is an Intranet.

7. The apparatus of claim 1, wherein said first and second lasers are each about 1.5 inches from the microbolometer.

8. The apparatus of claim 1, wherein each of said first and second lasers is aimed to emit light at an angle of about 85.24 degrees distally from said horizontal line.

9. The apparatus of claim 1, wherein said first and second lasers are positioned such that light emitted from said lasers crosses at a distance of about 18 inches distally from said microbolometer.

10. The apparatus of claim 1, wherein said trigger is adapted to have multiple engagement positions.

11. The apparatus of claim 10, wherein the trigger positions are selected from the group consisting of a laser on position, a camera on position, a microbolometer on position, an combination on position, and an all off position.

12. The apparatus of claim 1, wherein the means to communicate information to another electronic device comprises an electronic communication means selected from the group consisting of a USB connection, a flash drive, a Bluetooth connection, and a permanent computer cable.

* * * * *